Figure 1:
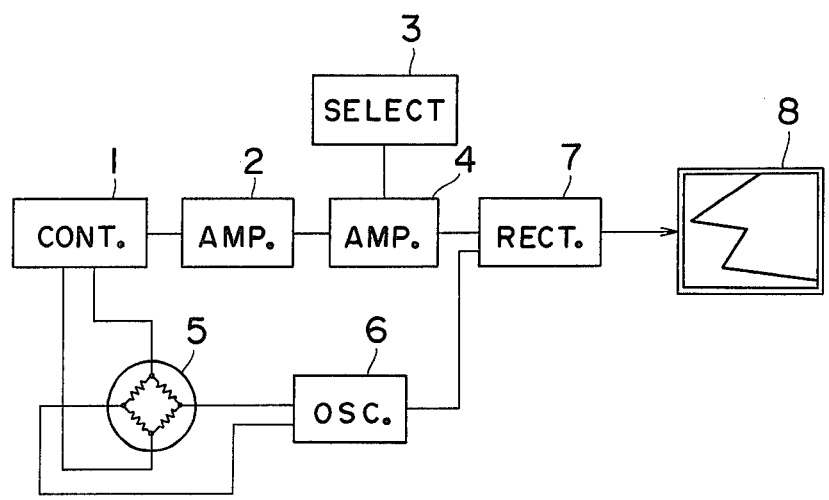
Figure 1:
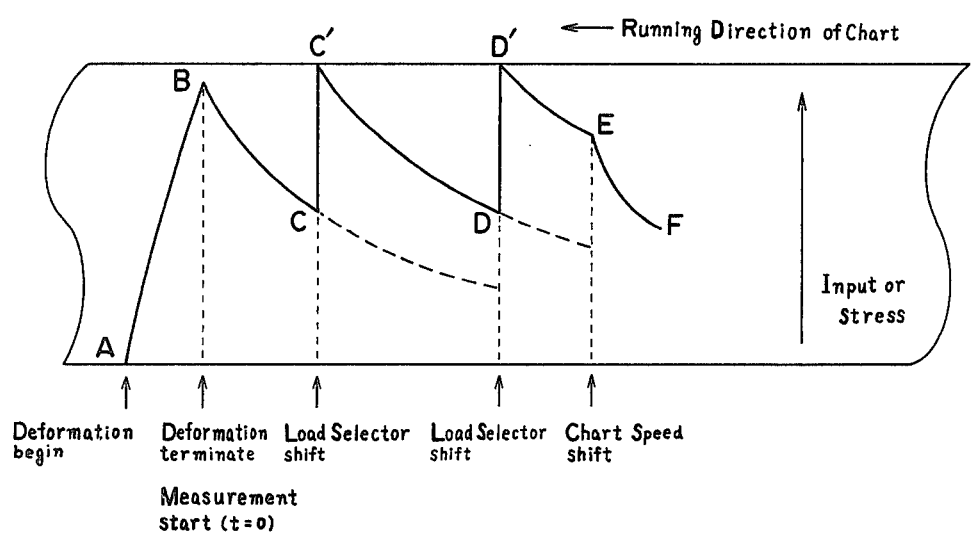

United States Patent [19]

Arai et al.

[11] 4,103,541
[45] Aug. 1, 1978

[54] METHOD OF AND A DEVICE FOR MEASURING A RELAXATION PHENOMENON

[75] Inventors: Kozo Arai; Teizo Kotani, both of Yokohama; Toshio Mizushima, Tokyo, all of Japan

[73] Assignee: Japan Synthetic Rubber Company Limited, Tokyo, Japan

[21] Appl. No.: 848,160

[22] Filed: Nov. 3, 1977

[30] Foreign Application Priority Data

Jan. 12, 1977 [JP] Japan .................................. 52-1431

[51] Int. Cl.$^2$ .......................... G01D 9/16; G01N 3/06
[52] U.S. Cl. .................................... 73/88 R; 73/15.6; 73/89
[58] Field of Search .................. 73/15.6, 88 R, 89, 94, 73/95

[56] References Cited

U.S. PATENT DOCUMENTS

| 2,647,393 | 8/1953 | Stewart | 73/15.6 |
| 3,134,256 | 5/1964 | Wolstenholme | 73/15.6 |
| 4,019,365 | 4/1977 | Woo | 73/15.6 |

OTHER PUBLICATIONS

R. D. Andrews, *Journal of Applied Physics*, vol. 26, No. 9, Sep. 1955, pp. 1061-1067.

M. Holt et al., *Journal of Basic Engineering*, Sep. 1970, pp. 655-661.

Scherr et al., *Journal of Applied Polymer Science*, vol. 7, 1963, pp. 1273-1279.

*Primary Examiner*—Charles A. Ruehl
*Attorney, Agent, or Firm*—James E. Nilles

[57] ABSTRACT

A method of measurement of relaxation phenomena, in which input signals representing a relaxation phenomenon are recorded at equal intervals for logarithmic values of time.

A measuring device for relaxation phenomena which comprises a logarithmic time pulse oscillator for producing pulse signals at equal intervals for logarithmic values of time, and a recorder for recording input signals representing a relaxation phenomenon converted into an electrical quantity, which operates to perform recording each time a pulse signal is produced.

3 Claims, 10 Drawing Figures

FIG. 4 (1)
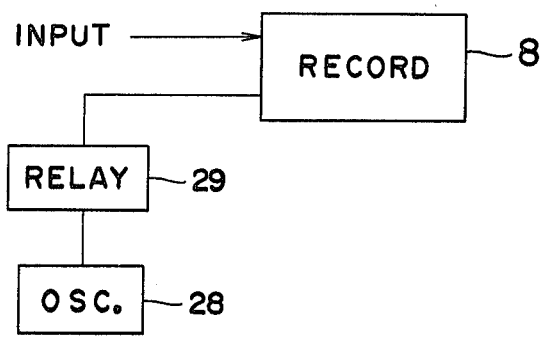
FIG. 4(2)
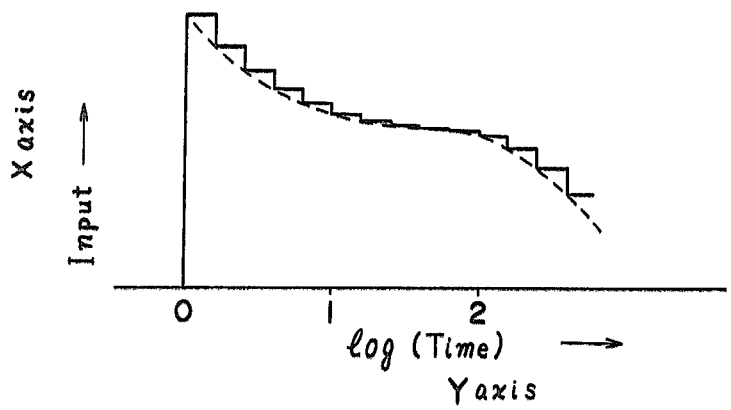
FIG. 5
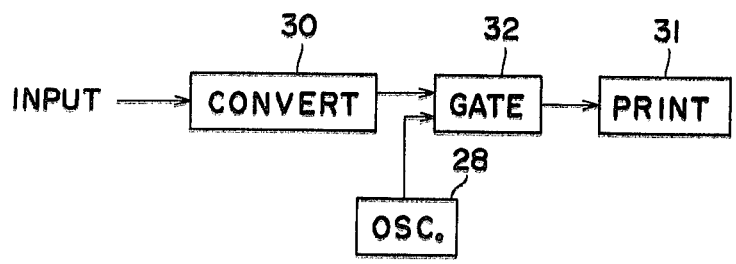

METHOD OF AND A DEVICE FOR MEASURING A RELAXATION PHENOMENON

The present invention relates to a method and a measuring device for making rational and accurate measurement of a relaxation phenomenon which progresses over an extremely long period.

The relaxation phenomenon described in the present invention generally implies a phenomenon wherein a change in the physical quantity of an object caused by a change in external conditions produces another equilibrium state with time lag. For instance, when a dynamically balanced object is subjected to an external force and deformation results, dispersion of energy normally takes place due to re-arrangement of molecules, and therefore, deformation is developed, lagging behind application of external force. This is the so-called creep phenomenon.

When a change in external conditions is strain instead of external force, the stress developed in an object caused by exactly the same reason mentioned above would give time lag to the strain. This is a stress relaxation phenomenon.

All of the examples given here are examples of mechanical relaxation phenomenon, and since these phenomena can noticeably be observed particularly in rubber or a plastic high-molecular substance, they are effectively utilized as one of the indexes representing mechanical features or states of said high-molecular substances.

The stress relaxation phenomenon implies, as mentioned already, "a time dependence in reduction in the stress which is developed when a given strain is applied to a sample". The phenomenon is one of the most well-known behaviors of a high-molecular substance, and progress has been made in accumulation of data based on a great number of measurements made since early times.

Hereinafter, description of a method of measurement of relaxation phenomenon and a measuring device for the measurement according to the present invention is made, taking a stress relaxation phenomenon as an example, and comparing with a conventional method.

A variety of shapes as well as modes of deformation are considered in the measurement of a stress relaxation phenomenon. An example of a conventional method of measurement is described, referring to FIG. 1.

First, in a balanced state as shown in FIG. 1(1), a load cell 5 is balanced by means of a balance control 1. Then, stress applied to the load cell 5 disturbs the balance of a bridge, causing ac voltage to be produced. The ac voltage is amplified by an amplifier 2 in the initial stage, and further amplified by an amplifier 4 in the following stage at an amplification ratio established by a load selector 3 as required before it is rectified by a rectifier 7 to be finally recorded by a recorder 8. An oscillator 6 is an ac power source for the load cell 5.

FIG. 1(2) shows an example of a chart indicating a relaxation phenomenon examined by such apparatus. In the figure, A represents a state immediately after the starting of application of strain to a sample. As the strain increases, an input fed to the recorder 8 grows larger in accordance with stress until it reaches B when the strain is fixed. Therefore, B indicates a starting point of measurement.

After that, the stress reduces and when it has reached a certain point C, the input will reach a point C' by means of changing the amplification degree, for instance, to double so as to double the electromotive force. The switching of the amplification degree has to be performed during measurement as required to maintain accuracy of measurement. Changes caused by the switching of the amplification degree are also indicated by D and D'. When further progress in the relaxation has reached as far as E, the chart velocity of the recorder 8 is slowed down to 1/n of the initial velocity. This is done because the analysis of the relaxation phenomenon is achieved not at equal intervals in terms of measuring time, but in the manner of geometrical progression, i.e., at equal intervals in terms of logarithm of time. The chart velocity is also required to be switched periodically during measurement.

Thus, the conventional method of measurement of a stress relaxation phenomenon is simple in its principle, however, it largely depends upon artifical selection including the selection of amplification degree, and the point as well as the degree of switching of the chart velocity, and moreover, it requires skillful manipulation.

Disadvantages of the conventional method of measurement may be boiled down to the following four clauses:

The first problem is the selection of an amplification degree and its switching frequency. That is, in the stress relaxation phenomenon, the stress is greatest in its initial value at the starting of measurement so that estimation of an appropriate amplification degree must be made in accordance with a value that has been presumed prior to the measurement in order to obtain a highly accurate result. Further, the degree of the consequent stress relaxation is greater in the initial stage, and therefore frequent switching is required to maintain an appropriate amplification degree.

The second problem is that the feeding velocity of the chart paper of the recorder must be successively reduced manually as the measuring time lapses for the reasons as mentioned already.

The third problem is that the obtained chart only shows a change in the relaxation phenomenon caused by lapse of time so that the chart must be divided by logarithmic time into equal intervals for analysis. This is concerned with the second problem, and it is because the relaxation phenomenon is generally interpreted as a function of logarithm of time, which is considered to be most rational.

The fourth problem is that the data must be accurately read and recorded.

Among these, the first and the fourth problems can be solved by the combined use of commercial devices such as an AD converter and a digital printer, which have high sensitivity and big effective figures. However, the second and the third problems can not be solved by the conventional techniques, and therefore, it is difficult to achieve rationalization as well as improvement of accuracy in the measurement of the stress relaxation phenomenon as a whole. As a matter of fact, if the first and the fourth problems are solved by the use of highly-sensitive AD converter and printer, and the second problem remains unsolved since the printer, unlike a recorder, does not usually have a function for changing recording speed. To be more specific, such problem remains unsolved that data are measured at equal intervals in time and therefore, a number of meaningless data over a long period after the middle period are inevitable when intervals of sampling time are chosen small, placing an emphasis on the initial period in the measurement, and on the other hand, when the emphasis is placed on the latter period, measuring frequency in the initial period would become low. In short, it is difficult to make highly accurate measurement over a long period by means of the conventional method.

It is an object of the present invention to provide a method of measurement and a device for the measurement whereby rational and highly accurate measurement of the relaxation phenomenon can be made, utilizing pulse singnals delivered from an oscillator which produces array of pulses at equal intervals for logarithmic values of time.

The inventors of the present invention have completed the present invention by the discovery that the use of an oscillator generating pulse signals at equal intervals for logarithmic values of time (hereafter referred to as logarithmic pulses) provides complete solution of the above-mentioned second and third problems in the measurement of the stress relaxation phenomenon. Further, it has been confirmed that combination of the logarithmic pulse oscillator with a solving means for the abovementioned first and fourth problems allow far more rational and accurate measurement of the stress relaxation phenomenon to be made compared with the conventional measurement.

Figure 2:
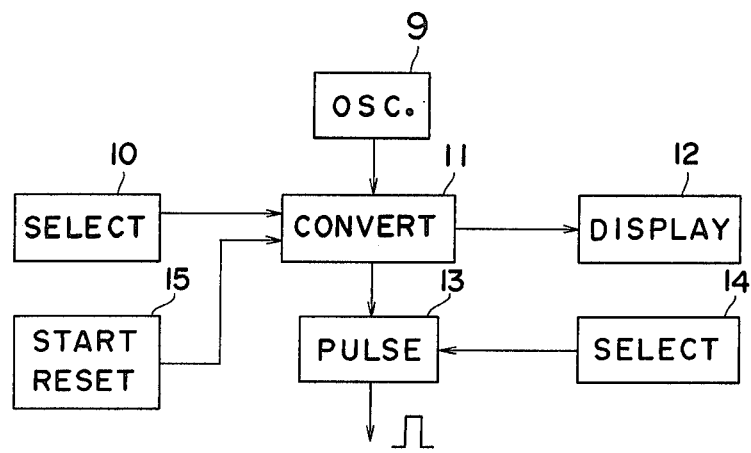
Figure 3:
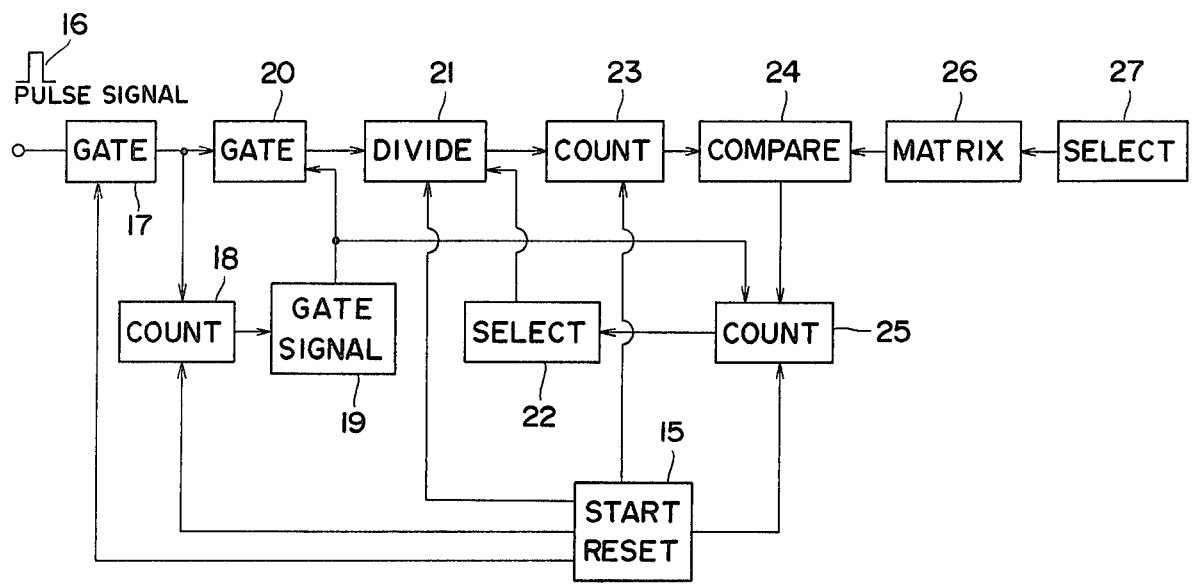
Figure 6:
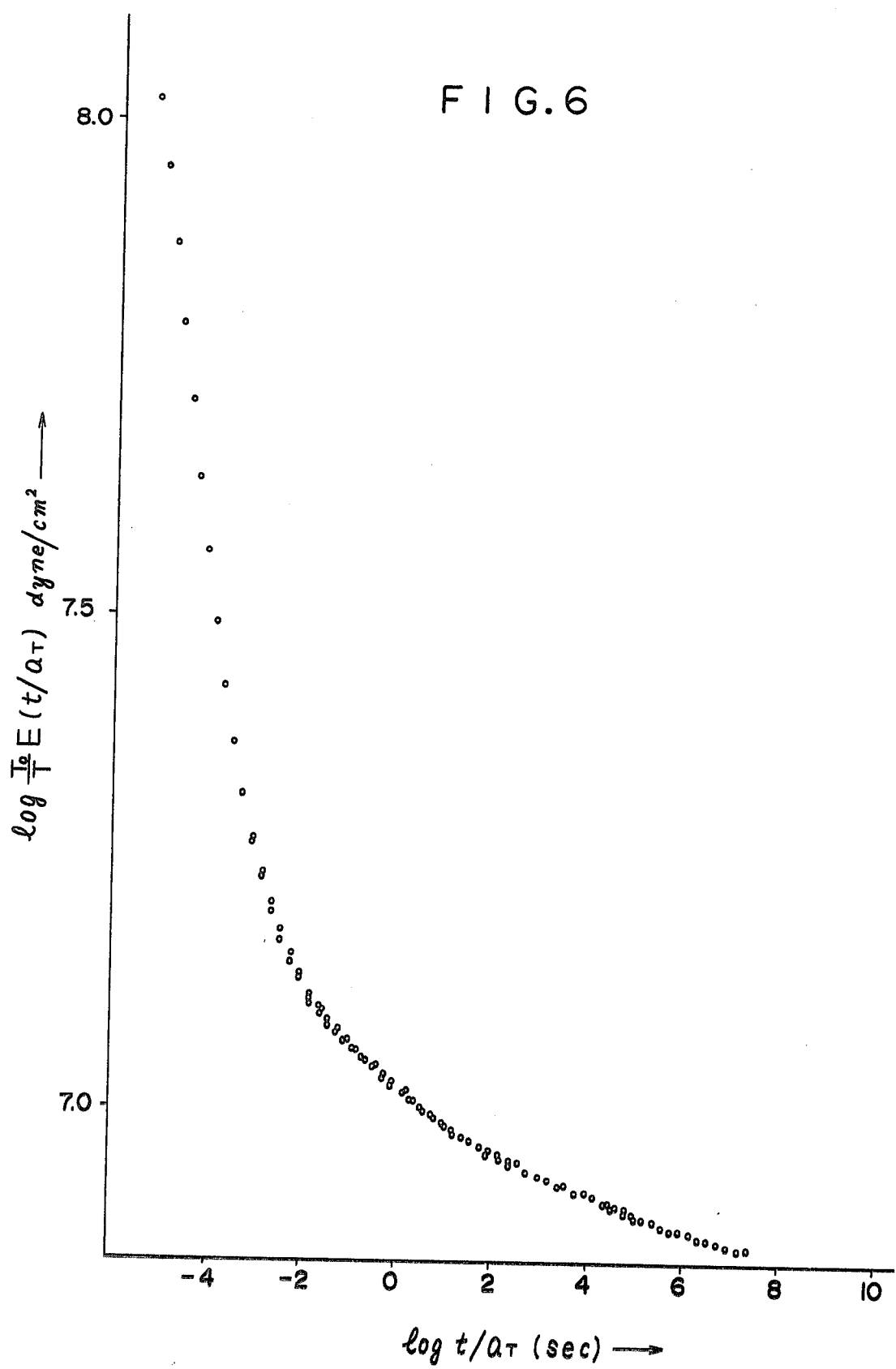
Figure 7:
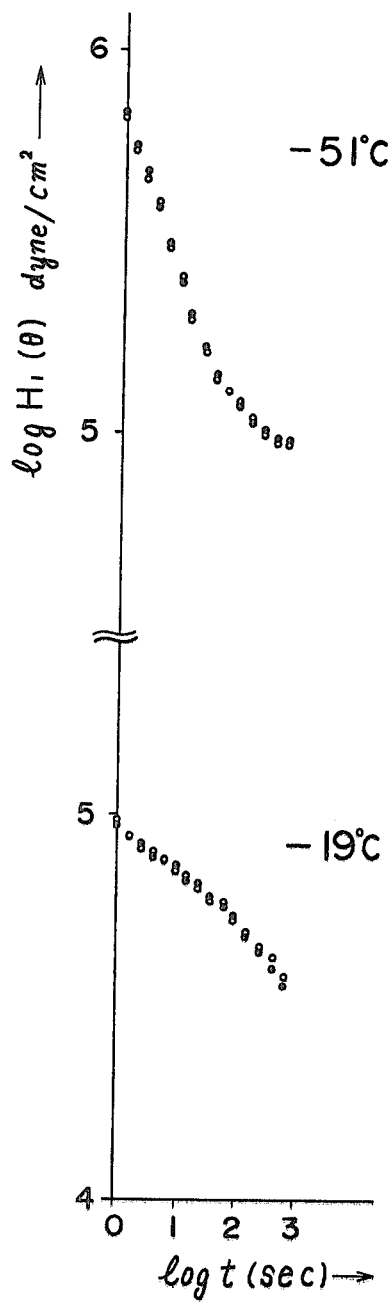
Figure 7:
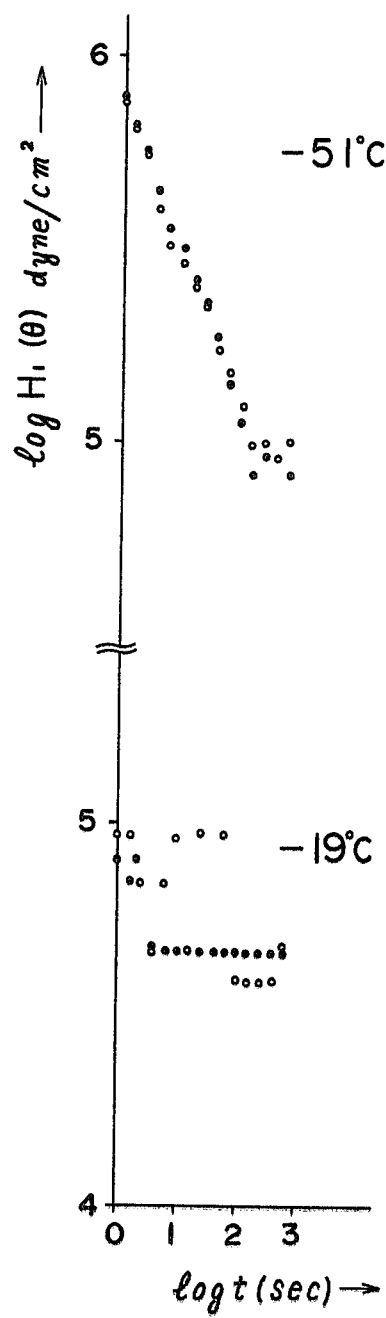

The nature of the present invention as well as other objects thereof will become more apparent from consideration of the following detailed description and the accompanying drawings in which:

FIG. 1(1) and FIG. 1(2) are a constitution diagram of the conventional measuring device of the stress relaxation phenomenon, and a typical diagram of an example of measurement made by said device, respectively, FIG. 2 is a block diagram of a device for generating spacing pulses, FIG. 3 is a block diagram of a logarithmic conversion circuit for said device, FIG. 4(1) and FIG. 4(2) are a diagram of the principal parts of an embodiment of a measuring device for the stress relaxation phenomenon according to the present invention, and a typical diagram of an example of measurement made by said device, respectively, FIG. 5 is a diagram of the principal parts of another embodiment of the device according to the present invention, FIG. 6 is a master plots of an example of actual measurement of the stress relaxation, which has been obtained by the present invention, and, FIG. 7(1) and FIG. 7(2) are plotting diagrams wherein the results of relaxation spectrum obtained by the method according to the present invention, and by the conventional method are compared in reproducibility and accuracy, respectively.

The device for generating spacing pulses shown in FIG. 2 mainly consists of a crystal oscillator 9 which performs accurate oscillation independently of changes in the environmental condition, a time selector 10 which specifies in advance the generating range of the time pulses from the crystal oscillator 9, a logarithmic conversion circuit 11 that repeats a process of dividing the number of pulses to compare the result with a specified value so as to convert it into a logarithmic value, a spacing selector 14 for specifying in advance the generating intervals of pulses, and a pulse generating circuit 13 for generating pulses in accordance with the designation made by the time selector 10 and the spacing selector 14, and also has accessory mechanisms, including a starting-resetting circuit 15 and an indicating part 12 for indicating logarithmic values of time.

The pulse signals generated by the pulse generating circuit 13 of the above device may be represented by the following formula:

$$\log t \text{ (sec)} = A + B$$

where $t$ indicates the time in seconds required for a signal to be generated since the starting of measurement, $A$ is a value of two figures (e.g. 0.0 - 6.0) indicated on said device, and $B$ is a coefficient representing the measuring range which is specified by the time selector 10. The generating interval $\alpha \log t$ of pulses delivered from the pulse generating circuit 13 may specify, for instance, either 0.1 or 0.2 by means of the spacing selector 14. The n-th pulse is generated in $10^{(n-1)\alpha \log t + B}$ sec. after a starting signal has been delivered.

Table 1 shows the measuring range.

Table 1

| t sec. | | | log t | Measuring Range B=−2 −1 0 1 |
|---|---|---|---|---|
| 0.01 | | | −2 | |
| 0.1 | | | −1 | |
| 1 | | | 0 | |
| 10 | | | 1 | |
| 100 | | 1 min. 40 sec. | 2 | |
| 1000 | | 16 min. 40 sec. | 3 | |
| 10000 | | 2 hrs. 46 min. 40 sec. | 4 | |
| 100000 | 1 day 3 hrs. 46 min. 40 sec. | | 5 | |
| 1000000 | 11 days 13 hrs. 46 min. 40 sec. | | 6 | |
| 10000000 | 115 days 17 hrs. 46 min. 40 sec. | | 7 | |

The generating time of pulses when $B=0$, $\Delta \log t=0.1$, and, $B=-2$, $\Delta \log t=0.2$, respectively, is indicated in Table 2.

Table 2

| B | 0 | | −2 | |
|---|---|---|---|---|
| Δ log t | 0.1 | | 0.02 | |
| log t, t | log t | t | log t | t |
| Pulse No. | | | | |
| 1 | 0.0 | 1.0000 | 0.0 | 0.010000 |
| 2 | 0.1 | 1.2583 | 0.2 | 0.015849 |
| 3 | 0.2 | 1.5849 | 0.4 | 0.025119 |
| . | . | . | . | . |
| . | . | . | . | . |
| . | . | . | . | . |
| n | $\frac{n-1}{10}$ | $10^{n-1/10}$ | $\frac{n-11}{5}$ | $10^{n-11/5}$ |

Hereafter, description is made for the logarithmic conversion circuit 11 employed by the device in accordance with the present invention, referring to FIG. 3.

(1). An input pulse signal 16 passes through an input gate 17 controlled by the starting-resetting circuit 15, and then is added to an initial-value counter 18 and an integrating gate 20.

(2). The initial-value counter 18 activates a gate signal generating circuit 19 to open the integrating gate 20 and to make a logarithmic-value counter 25 become zero when the input pulse signals 16 of a specified number have entered.

(3). When the integrating gate 20 is opened, the input pulse signals 16 are integrated by an integrating counter 23 through a frequency-dividing circuit 21. The frequency-dividing circuit 21 is controlled by a frequency-dividing selector 22 and it divides the input pulse signals 16 in the manner of 1, 1/10, 1/100, . . . . . . . . . as the indicated value of the logarithmic-value counter 25 changes as 0, 1, 2, . . . . . . . . . , i.e. the counting is performed, dropping the input pulse signals by one figure when a logarithmic value is increased by 1.

(4). In a diode matrix 26, there is a value of the step number of a mantissa, which has been acquired by subtracting a specified number determined by the initial-value counter 18 from an antilogarithm corresponding to the mantissa. A matrix selector 27 is activated by means of a value of the mantissa of the logarithmic-value counter 25, and a corresponding value is read out.

(5). A comparison circuit 24 parallelly compares the content of the integrating counter 23 with that of the diode matrix 26, and when they coincide with each other, it increases the mantissa of the logarithmic-value counter 25 by 1 step.

According to the present invention, a logarithmic pulse oscillator 28 is provided to be connected to a relay which maintains operation for one second, for example, every time a pulse signal is received so as to supply driving power to a driving motor (not illustrated) for the chart paper of an ordinary X T recorder 8 to which electric signals representing relaxation phenomenon are fed as input signals only while said relay 29 is in operation.

In the device according to the invention, the chart paper of the recorder 8 remains undriven unless it is driven for 1 sec. each time a pulse signal is delivered from the logarithmic pulse oscillator 28, while inputs are constantly fed to the recorder 8, and therefore, a resultant chart will provide a terraced diagram having an axis of time (T axis) indicating equal intervals, and the other axis (X axis) representing variation in the quantity of signals as shown in FIG. 4(2). Accordingly, connection of the initial point of each stage will form a relaxation curve (shown in a broken line). This method provides complete solution for the third problem among those problems described as disadvantages of the conventional technique, since a chart paper is driven at equal time intervals logarithmically. The fourth problem can not be solved completely as visual reading is required, but still this method according to the present invention will provide a suitable method in such cases where accuracy in measurement is not so important, or visual observation of the whole state of relaxation is desired.

FIG. 5 shows another embodiment of the device according to the present invention. In the present embodiment, input signals are converted to digital signals by an AD converter 30, and the digital signals are supplied to a digital printer 31 for recording only while a gate 32 is opened by the logarithmic pulse signals from the logarithmic pulse oscillator 28. This means that the logarithmic pulse signals sent from the logarithmic pulse oscillator 28 are utilized as printing command signals in the present embodiment. The gate 32 is located between the AD converter 30 and the digital printer 31 in the present embodiment, however, it may be located immediately before the AD converter 30. In the former case, input signals constantly undergo digital conversion at a conversion velocity which is characteristic of the AD converter, and printed on a printer 31 only when a pulse signal is delivered from the logarithmic pulse oscillator 28, while in the latter case, the input signals are digitally converted to be immediately printed only when a said pulse signal is delivered.

By the device shown in FIG. 5, the printed data representing the stress relaxation phenomenon are given as a function of the logarithm of time required for analysis as they are and also the generating intervals of pulse signals can be set in advance in accordance with an object of an experiment, thus providing necessary and satisfactory rational data.

Further, it is possible to improve measurement accuracy by achieving improvement in the accuracy of the AD converter 30.

Further, a memory may be located between the gate 32 and the printer 31 to make temporary storage of data, thereby enabling the measurement of a short period to be achieved independently of the recording speed of the printer.

Thus, the use of the logarithmic pulse oscillator 28 eliminates the process of dividing data into equal intervals for logarithmic time, which is indispensable to the anlysis made by the conventional method, and adoption of the digital printer 31 not only eliminates the time required for analyzing data, and processes requiring any skill, but also assures elimination of errors that may accompany them, resulting in significant rationalization in both measurement and analysis to be achieved.

The epochal method and device according to the present invention for making measurement of the stress relaxation phenomenon are not limitedly used only for this, but also can be rationally used for making measurement of all types of relaxation phenomena, including volume relaxation, dielectric relaxation, acoustic relaxation, magnetic relaxation, and nuclear magnetic resonance absorption spectrum.

Now, description is made for the measurement result of the stress relaxation phenomenon of a plyisoprene cured by a peroxide (dicumyl peroxide).

FIG. 6 shows a master curve having $-19.2°$ C as a reference temperature for reduced variables of the stress relaxation from $-62°$ C up to $49.4°$ C, which has been obtained by the method according to the present invention. In the diagram, $E(t/aT)$ is a relaxation modulus, and $T_o$ is a reduced temperature for reduced variables, and it is apparent from this diagram that considerably smooth shift is available, enabling a method of reduced veriables to be established. The variation in a plotting diagram of a result obtained by the conventional method would be far wider than that obtained by the method according to the present invention, and it reaches as far as max. 0.05 approximately on the logarithmic scale under the same conditions. The plotting diagram of the result obtained by the conventional method is omitted since it would become too complex.

The variation in such diagrams can be considered to represent comparative superiority in the method of measurement including analyzing ability of measurement, and to make it more apparent, comparison is made by a relaxation spectrum $H_1(\theta)$ which is defined by the following formula:

$$H_1(\theta) = \frac{T_o}{T} \{E(t_i) - E(at_i)\} (lna)^{-1} \Big|_{t = \theta X_1(a)}$$

where $T_o$ and $T$ are a reference temperature for reduced variables and a measuring temperature, respectively, $E(t_i)$ is a relaxation modulus at a time $t_i$, $a$ is a constant representing the time interval of data, and $X_1(a)$ is a constant absolutely determined by $a$. When $a = \sqrt[5]{10}$, $(lna)^{-1}$ and $X_1(a)$ will be 2.172 and 0.787, respectively. $\theta$ is relaxation time.

$H_1(\theta)$ is an index of distribution of the relaxation time, and it is greatly influenced by the variation of the relaxation modulus.

FIG. 7(1) and FIG. 7(2) show values of $H_1(\theta)$ at $-51°$ C and $-19°$ C. FIG. 7(1) represents a result obtained by the method according to the present invention, while FIG. 7(2) shows a measuring result obtained by the conventional method. These diagrams also show the results of repetition of the same measurement for the purpose of confirmed reproducibility of measurement. The white circular marks (○) show the results of the first measurement, and the black circular marks (●) the second measurement carried on the same sample. As may be known from these diagrams, by the conventional method, reasonably high reproducibility and accuracy can be obtained at $-51°$ C where relaxation velocity is high, but at $-19°$ C where the relaxation velocity is low, the reproducibility as well as accuracy are lost, resulting in a totally unreliable data.

On the other hand, the results obtained by the method according to the present invention invariably maintain sufficient accuracy and reproducibility regardless of the relaxation velocity, and therefore may satisfactorily be analyzed as they are.

Thus, the present invention provides, by means of a considerably simple method or a device of simple constitution, great benefits such as easy and yet highly reliable acquisition of measurement results of various relaxation phenomena, consisting of data of measuring points that are equal in time intervals directly logarithmically, said data deing allowed to be analyzed as they are with consequent significantly accurate results.

What is claimed is:

1. A method of measurement of relaxation phenomena, whereby pulse signals are generated at equal intervals for logarithmic values of time by means of a logarithmic time pulse oscillator, and input signals representing a relaxation phenomenon are recorded every time said pulse signal is delivered.

2. A measuring device for relaxation phenomena which comprises a logarithmic time pulse oscillator for producing pulse signals at equal intervals for logarithmic values of time, and a recorder for recording input signals representing a relaxation phenomenon converted into an electrical quantity, which operates to perform recording each time a pulse signal is produced.

3. A measuring device for relaxation phenomena as claimed in claim 2, wherein an AD converter is provided for converting input signals which represent a relaxation phenomenon into digital signals, and the recorder is of a digital recorder.

* * * * *